United States Patent
de Urquiza et al.

(10) Patent No.: US 6,355,446 B1
(45) Date of Patent: Mar. 12, 2002

(54) DOCOSAHEXAENOIC ACID AS RETINOID X-RECEPTOR LIGAND AND USES THEREOF

(75) Inventors: Alexander Mata de Urquiza; Thomas Perlmann; Maria Sjöberg; Liu Suya; Jan Sjövall; William Griffiths; Rolf Zetterstrom, all of Stockholm (SE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/534,774

(22) Filed: Mar. 24, 2000

(51) Int. Cl.$^7$ .................. G01N 33/53; G01N 33/567; G01N 33/574
(52) U.S. Cl. ................ 435/7.8; 435/7.2; 435/7.21; 435/7.23
(58) Field of Search ................ 435/7.2, 7.21, 435/7.23, 7.8

(56) References Cited

U.S. PATENT DOCUMENTS

| | | | |
|---|---|---|---|
| 5,399,586 A | * 3/1995 | Davies et al. | 514/448 |
| 5,747,661 A | * 5/1998 | Evans et al. | 536/24.1 |
| 5,766,571 A | * 6/1998 | Ceriani et al. | 424/1.49 |
| 5,854,292 A | * 12/1998 | Ailhaud et al. | 514/725 |
| 5,925,669 A | * 7/1999 | Katz et al. | 514/449 |
| 5,972,881 A | * 10/1999 | Heyman et al. | 514/3 |

OTHER PUBLICATIONS

I. Issemann et al.; The peroxisome proliferator–activated recetor:retinoid X receptor heterodimer is activated by fatty acids and fibrate hypolipidaemic drugs ; 1993; pp. 47.*

Haisu Wan et al.; Overexpressed Activated Retinoid X Receptors Can Mediate Growth Inhibitory Effects of Retinoids in Human Carcinoma Cells; Oct. 9, 1998, pp. 26915–26922.*

Balkan, et al., "Transgenic indicator mice studying activated retinoic acid receptors during development,"Proc. Natl. Acad. Sci. USA 89: 3347–3351 (Apr. 1992).

Lemon, et al., "Selective Effects of Ligands On Vitamin $D_3$ Receptor and Retinol X Activation In Vivo,"Mol & Cell Biol 16(3):1006–1016 (March 1996).

Wang, et al., "Ligand–Inducible and Liveer—Specific target gene expression in transgenic mice,"Nature Biotechnol 15: 239–243 (March 1997).

Solomin, et al., "Retinol–X Receptor Signaling In The Developing Spinal Cord,"Nature 395: 398–402 (Sep. 1998).

* cited by examiner

Primary Examiner—Prema Mertz
Assistant Examiner—Joseph F. Murphy
(74) Attorney, Agent, or Firm—Fulbright & Jaworski, LLP

(57) ABSTRACT

This invention involves the identification of a ligand for the retinol X receptor. Specifically docosahexaenoic has been identified as an RXR ligand. Various assays based upon this observation are a feature of this invention.

6 Claims, 4 Drawing Sheets

DOCOSAHEXAENOIC ACID AS RETINOID X-RECEPTOR LIGAND AND USES THEREOF

FIELD OF THE INVENTION

This invention relates to the retinoid X receptor, referred to hereafter as "RXR." More particularly, it relates to the identification of its ligands, and the ramifications of this identification.

BACKGROUND AND PRIOR ART

The nuclear receptor (NR) superfamily comprises more than 150 different proteins, most of which are believed to function as ligand activated transcription factors, exerting widely different biological responses by regulating gene expression (for review, see Di Croce et al, EMBO J1 8:6201–6210 (1999); Mangelsdorf, et al Cell 83:825–839 (1995); Perlmann, et al, Cell 90:391–397 (1997)). Members of this family include receptors for endogenous small, lipophilic molecules, such as steroid hormones, retinoids, vitamin D and thyroid hormone. In addition, many members of this family lack known ligands and are therefore referred to as "orphan receptors" (for review, see Gigère, et al, Endocrine Rev 20:689–725 (1999); Kastner, et al, Cell 83:859–869 (1995)).

During recent years small, lipophilic ligands and activators have been identified for several orphan receptors, leading to new insights of profound impact. These findings have dramatically increased understanding of endocrinology and disease (Forman, et al Cell 81:687–693 (1997); Xu, et al, Mol. Cell 3:397–403 (1999); Makashima et al., Science 284:1362–1365 (1999); Parks et al., Science 284:1365–1368 (1999); Wang et al., Mol Cell 3:543–553 (1999); Janowski et al., Nature 383:728–731 (1996); Kliewer et al., Cell 92:73–82 (1998); Blumberg et al., Genes Dev. 12:31953205 (1998)); however, ligands and biological functions of most orphan receptors remain to be elucidated, emphasizing the importance of unraveling previously uncharacterized signaling pathways by identifying novel endogenous ligands for NRs (for review, see Mangelsdorf et al, Cell 83:841–850 (1995); Giguère, et al, supra.

The retinoid X receptor (RXR) is activated by the vitamin A metabolite 9-cis retinoic acid, which binds with high affinity to the RXR ligand binding domain. In addition, RXR has been shown to form heterodimers with a large number of NRs including the retinoic acid receptor (RAR) and several orphan receptors. RXRs are essential for development of the embryo as shown by gene ablation experiments. In addition, genetic analyses of mutant mice have indicated important functions in the adult, e.g. in the central nervous system.

Dietary fatty acids have long been recognized as essential for normal growth and development, as energy fuels, membrane components and as precursors of essential lipidmetabolites (Salem et al., In Health Effects of Polyunsaturated Fatty Acids in Seafoods (1986); Neuringer et al., Ann Rev Nutr 8:517–541 (1998); Horrocks et al, Pharmacological Res 40:211–225 (1999); Xiang and Zetterstrom, Acta Paediatr 88:78–82 (1999)). Fatty acids are classified as "non-essential" and "essential," respectively. Essentially fatty acids cannot be synthesized in humans and must be taken up via the diet. These include linoleic acid (18:2n–6), alpha-linolenic acid (18:3n–3), and their elongation and desaturation products arachidonic acid (20:4n–6) and docosahexaenoic acid (DHA; 22:6n–3), respectively (for a description of fatty acid nomenclature, see e.g. Neuringer et al., supra. Arachidonic acid has been shown to be the major precursor of eicosanoids, a large family of biologically active factors including prostaglandins, prostacyclins, leukotrienes and hydroxy fatty acids. These metabolites act as chemical transmitters both within and between cells, and have been shown to regulate ion transport, hormone secretion and the immune response. Interestingly, several arachidonic acid metabolites and other fatty acids have been shown to function as ligands for peroxisomeproliferator activated receptors, demonstrating that they can function as mediators of NR signaling cascades, in vivo.

In contrast to arachidonic acid metabolites, the mechanism(s) of action of DHA is not well understood. Interestingly, DHA accumulates at high levels in the postnatal mammalian CNS indicating that DHA is involved in the maturation of the CNS and/or in neurological processes. Notably, DNA deficiencies lead to neurological abnormalities and diminished learning ability in man (see Gamoh, et al, Neurosci 93:237–241 (1999); Fernstrom, Lipids 34:161–169 (1999); Sheaff Greiner, et al, Lipids Suppl 34:239–243 (1999)). Moreover, dietary DHA may be beneficial in treatment of atherosclerosis, inflammation and cancer (Horrocks, et al, Pharmacol Res 40:211–225 (1999); Rose, et al, Pharmacol Theraput 83:217–244 (1999)).

It has now been ascertained that DHA functions as a ligand for RXRs. As is elucidated herein, DHA may exert its biological activities, in whole or in part, by way of activating RXRs. This pathway has not been described in the prior art, and is a feature of the invention, as will be elucidated herein.

DETAILED DESCRIPTION OF PREFERRED EMBODIMENTS

EXAMPLE 1

This example describes experiments designed to determine the existence of endogenous retinoid receptor ligands in vivo. To do this, cells from human choriocarcinoma cell line JEG-3 were cotransfected with a UAS luciferase reporter construct and an expression vector. The expression vector was either pCMX-GAL4-RAR or pCMX-GAL4-RXR. The expression vectors contained a construct which encoded the yeast GAL4 binding domain (amino acids 1–147), cloned in frame to the ligand binding domain of either human RAR or human RXR. Transfection was carried out, in triplicate, in 24 well plates using the calcium phosphate method of Perhnann, et al., Genes Dev 9:769–782 (1995), incorporated by reference. Each well was transfected with 100 ng of the UAS luciferase reporter construct, 100 ng of the expression plasmid, and 200 ng of a reference plasmid, i.e., pCMX-βgal, containing a bacterial β-galactosidase gene. Cells were cultured and, following 6–8 hours of transfection, fresh medium supplemented with 10% charcoal stripped fetal calf serum, 1% penicillin/streptomycin and 1% L-glutomine were added, together with mouse tissue explants, as explained infra.

Mouse tissue explants provide a potential source of endogenous ligands, and were used in these assays. To secure these, adult, wild type NMRI mice were perfused via their ascending aortas with cold phosphate buffered saline in order to remove blood from vessels. Organs were dissected out, razor cut to small pieces, and placed in minimum essential medium. Embryonic tissues were collected from wild type (E13.5) embryos in the same way. Tissues were then either placed directly on the transfected cells, or incubated in medium overnight, at 37° C. Conditioned medium was then separated from the tissue, and frozen in aliquots, until assayed on transfected cells. The results are depicted in FIG. 1.

Figure 1B:
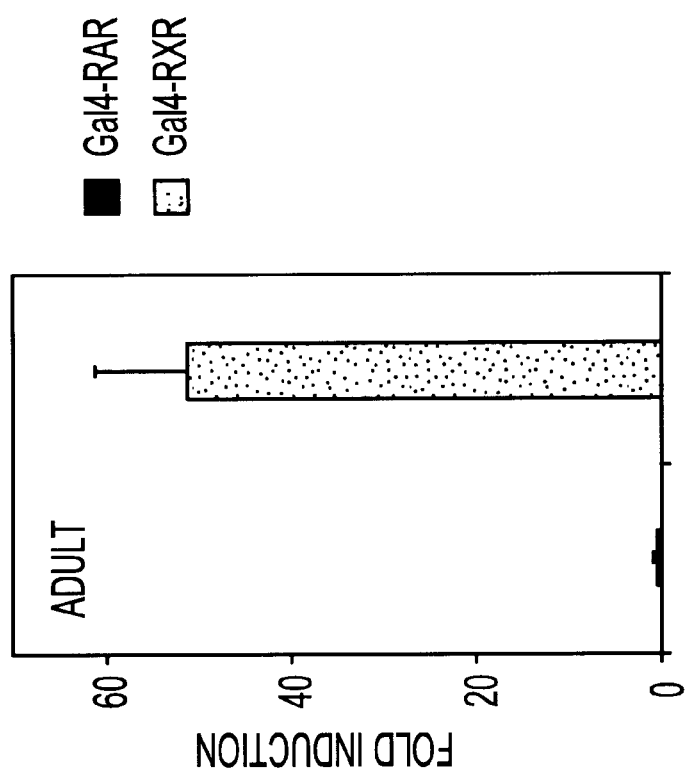
FIGS. 1A and 1B show that the activation of GAL4-RAR and GAL 4-RXR constructs by conditioned medium from murine explants is developmental stage specific.
Figure 1A:
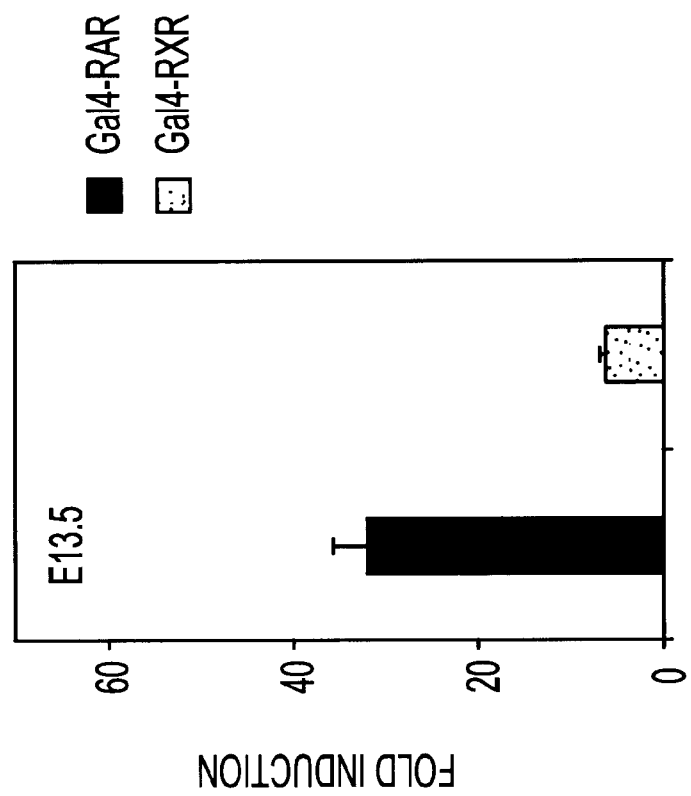

It was found that embryonic CNS contained a ligand which activated RAR, i.e., E 13.5. embryonic spinal cord and brain conditioned mediaboth activated GAL4-RAR, but not GAL4-RXR as shown in FIG. 1A. It was notable that the opposite result was obtained using adult CNS tissue as shown in FIG. 1B. For example, conditioned medium obtained from brain tissue of 8 week old mice activated GAL-RXR, but only modestly increased activity of GAL4-RAR.

EXAMPLE 2

RXR is a common heterodimerization partner of many nuclear receptors. The following experiments were designed to determine if the adult brain conditioned medium activated the RXR ligand binding domain directly, or activated a heterodimerizing partner of RXR, expressed in transfected, JEG-3 cells.

The experiment used constructs which encode the ligand binding domain of receptor Nurr-1, an orphan nuclear receptor that heterodimerizes with RXR. RXR is a permissive heterodimerization partner in RXR-Nurr1 heterodimers, and is efficiently activated by ligand when in such complexes. paralleling those described supra, i.e., pCMX-GAL4-NURR1 were used as bait, and expressed together with wild type RXR using construct pCMX-RXR in JEG-3 cells. The same assay as is described, supra was used. Contransfection of GAL4-Nurr1 or RXR expression vectors together with the UAS -luciferase reporter plasmid resulted in efficient activation by brain conditioned medium. Incontrast, when wild-type RXR was not co-transfected with the GAL4-Nurr1 vector, only modest activation was observed, presumably due to heterodimerization between overexpressed GAL4-Nurr1 and exogenous RXR. These data provide evidence that RXR is the direct target of the adult brain-derived activity.

Figures 2A, 2B:
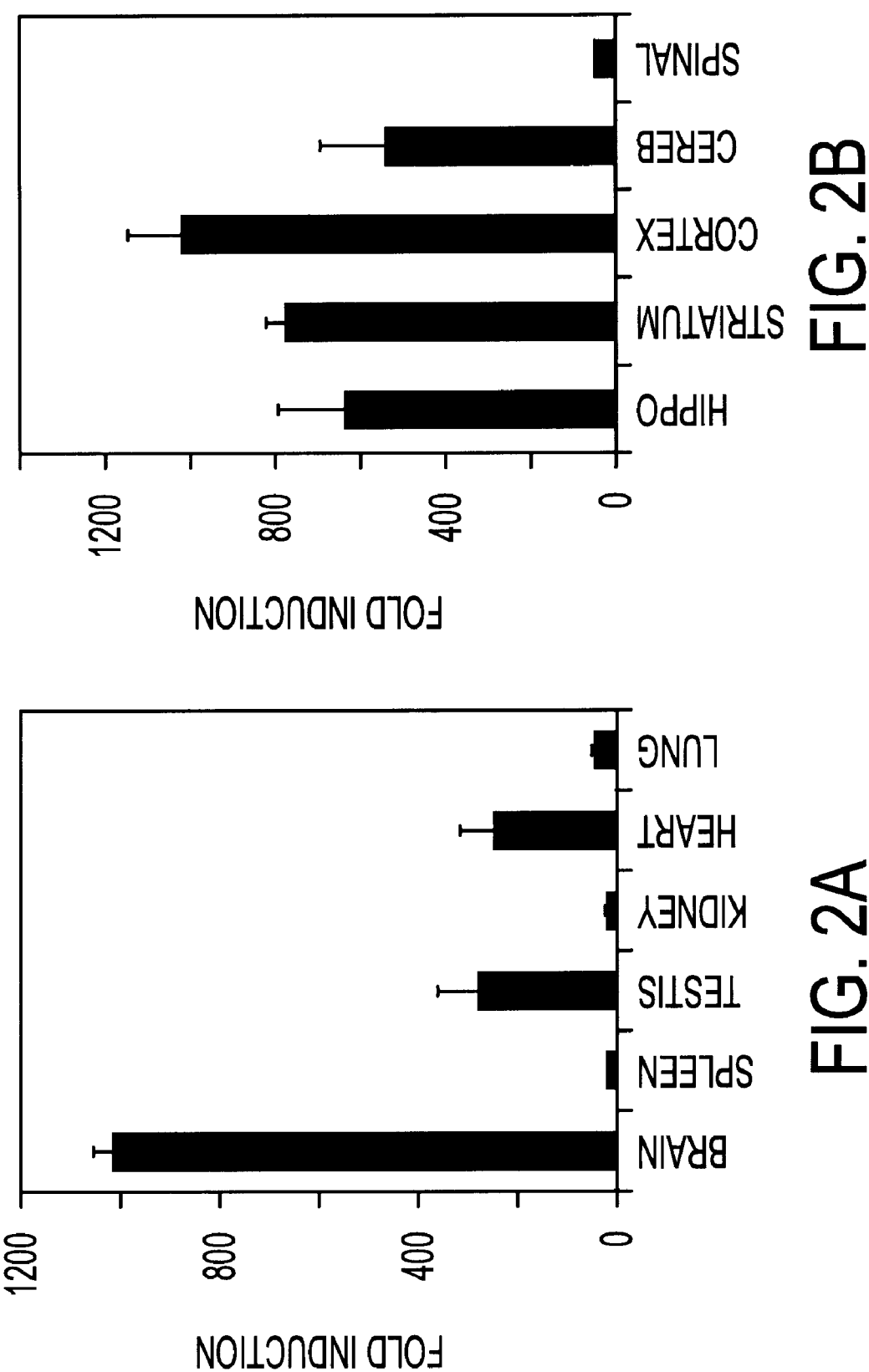
FIG. 2 presents data comparing conditioned media from different tissue sources.

Additional experiments were carried out to examine the effect of media conditioned with explants from peripheral tissues, i.e., could these activate GAL4-Nurr1/RXR. The results are depicted in FIG. 2. Media from testes and heart activated the reporter 250–300 fold, with modest activity in CM from spleen, kidney, and lung. Brain conditioned medium activated the reporter most strongly. These results suggested following up with experiments using adult brain, and central nervous system conditioned medium.

When adult central nervous system tissue was investigated, medium that had been conditioned from hippocampus gave the strongest signal, as compared to striatum, motor cortex, cerebellum and spinal cord tissue. Activity was observed throughout, however, suggesting broad distribution of the RXR activating factor within the brain, as shown in FIG. 2.

EXAMPLE 3

These experiments describe additional work on isolating the ligand. Brain conditioned medium was mixed with an equal volume of hexane, and shaken vigorously for five minutes. The mixture was centrifuged, for 10 minutes at 12,000 rpm to separate phases, after which the upper phase was removed to a clean tube. Extraction of the aqueous phase was repeated, and the two resulting organic phases were pooled. Hexane extracts were then evaporated under nitrogen gas. Residues were redissolved in small amounts of pure ethanol, and tested, as described supra.

In parallel, media were pretreated with hydrochloric acid. The results, indicate that the pretreatment with hydrochloric acid increased yields, suggesting that the active material is a lipophilic, negatively charged molecule.

EXAMPLE 4

Further experiments were carried out to purify the active component to homogeneity. To elaborate, the hexane extract of conditioned medium was evaporated, and the residue was redissolved in 200 ml of hexane. Samples (150 mls) were injected onto a normal phase HPLC column, and elution was performed using a linear gradient from hexane to hexane/dichloromethane/isopropanol (85:10: 5 v/v), both of which contained 1% acetic acid for 30 minutes at a flow rate of 0.5 ml/min. After 17 minutes following the injection 30 fractions, each of which contained 0.25 ml of sample, were collected. Fractions were tested using the assay described supra. The active fractions were pooled, evaporated to dryness, redissolved in 50 μl of 80% methanol, and a 30 μl sample was injected onto a reversed phase HPLC column. A mobile phase of methanol/isopropanol/water (80:10:10 v/v), containing 1% acetic acid, at a flow rate of 0.3 ml/minute, was used. Again aliquots were tested on transfected JEG-3 cells, as described supra.

Active fractions were subjected to nano-electrospraymass spectrophotometric analysis. The results indicated that the active molecule had a chemical formula of $$C_{22}H_{31}O_2$$

On the assumption that the molecule was a deprotonated ion, the formula of the active compound is $$C_{22}H_{32}O_2$$

This is the formula of docosahexaenoic acid. Collision induced dissociation spectra of the [M–H]–ion of cis 4, 7, 10 13, 16, 19-DHA was compared to the active fraction, and they were remarkably similar, leading to the conclusion that the active molecule is cis–4, 7, 10, 13, 16, 19-DHA

EXAMPLE 5

In view of the results presented supra, various polyunsaturated fatty acids were tested, to determine if they would activate the reporter genes, in cells cotransfected with GAL4-Nurr1 and RXR expression vectors. Specifically, 20 uM of individual polyunsaturated fatty acids were added to the cells, and activity was measured as described, supra. The polyunsaturated fatty acids tested were linoleic acid (18:2), linolenic acid (18:3), arachidonic acid (20:4), heneicosadienoic acid (21:2); behenic acid (22:0); docosadienoic acid (22:2); docosatrienoic acid (22:3); docosatetraenoic acid (22:4); docosapentaenoicacid(22:5); docosahexaenoicacid (22:6); andmethylateddocosahexaenoic acid (22:6 met).

Figure 3A:
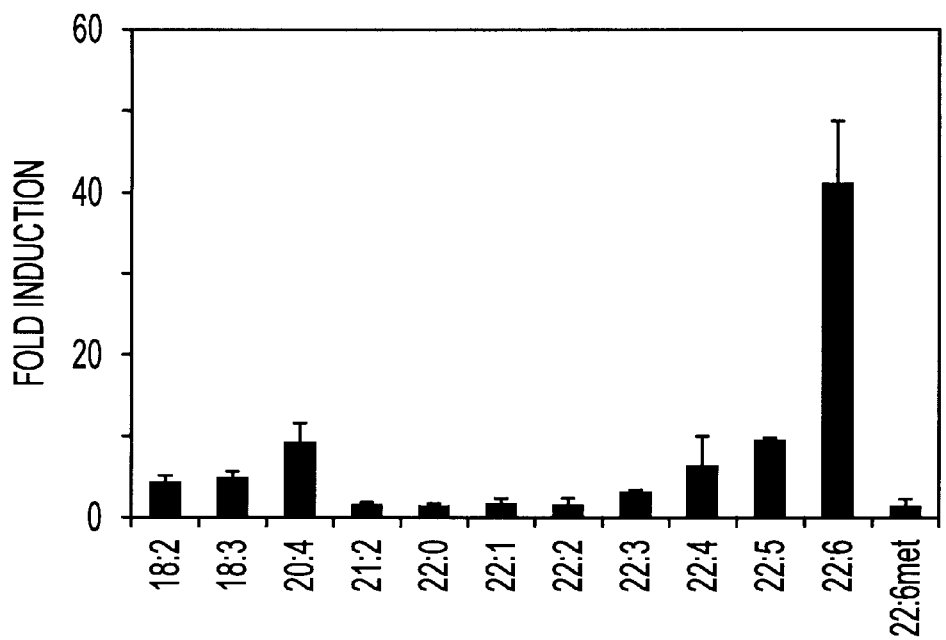
FIGS. 3A & 3B depict data comparing different polyunsaturated fatty acids and their activating effect on RXR (3A), and varying concentrations and their effect (3B)

The results are depicted in FIG. 3A, and show that docosahexaenoic induced robust activiation, while the other molecules tested showed modest activity.

Figure 3B:
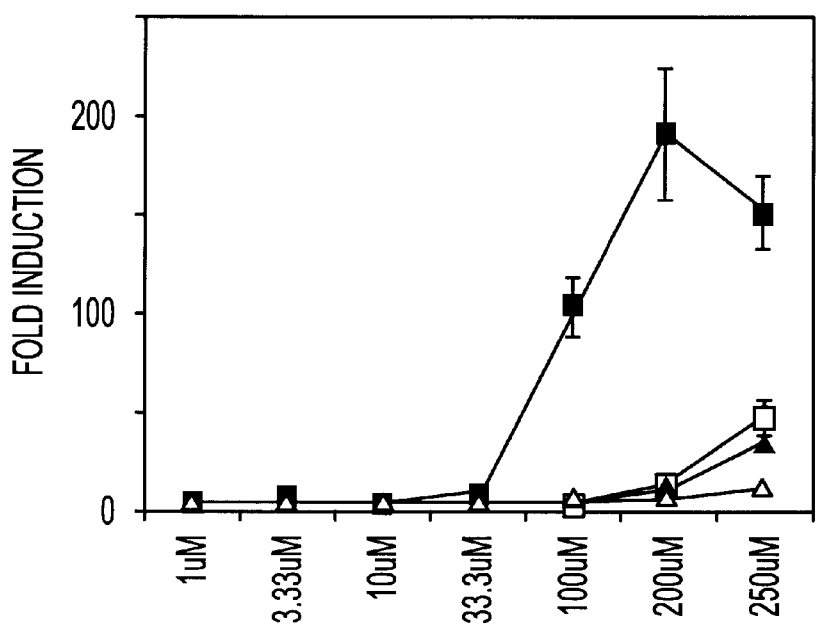

In follow up experiments, varying concentrations of DHA, linolenic acid, linoleic acid, and oleic acid were tested (1 uM to 250 uM). The results are presented in FIG. 3B, as fold induction after normalization and comparison to the β galactosidase control. These follow up experiments indicated that DHA is the most efficient activator, showing EC50 at approximately 30 uM.

EXAMPLE 6

The experiments described herein were designed to determine if DHA mediates its effect by direct ligand binding to the ligand binding domain of RXR. It is known that ligand activated NRs associate with coactivators, including the molecule known as SRC-1. To do this, the ligand binding domains of human RXR and murine ER were expressed as GST fusion proteins in E. coli, in accordance with Cavailles, et al, Proc. Nat. Acad. Sci USA 91(21):10009–13 (1994) were bound to glutathione—sepharose beads, while a construct based upon Psa5, which contained cDNA for SRC-1e was used to generate [$^{35}$S] methionine labelled proteins, using a commercially available system.

[$^{35}$S] labelled SRC-1 proteins were incubated, with beads labelled with either GST, or GST fusion protein, in the presence of DMSO, 1 μM estradiol, or DHA, at varying concentrations, in an NETN buffer (0.5% NP-40, 20 mM Tris-HCl, pH 8.0, 100 mM NaCl, 1 mMEDTA), and protease inhibitors. The mixtures were incubated overnight, and free proteins were washed away from the beads with NETN buffer. Bound proteins were eluted in loading buffer, separated by SDS-PAGE, and visualized by fluorography.

Figure 4:
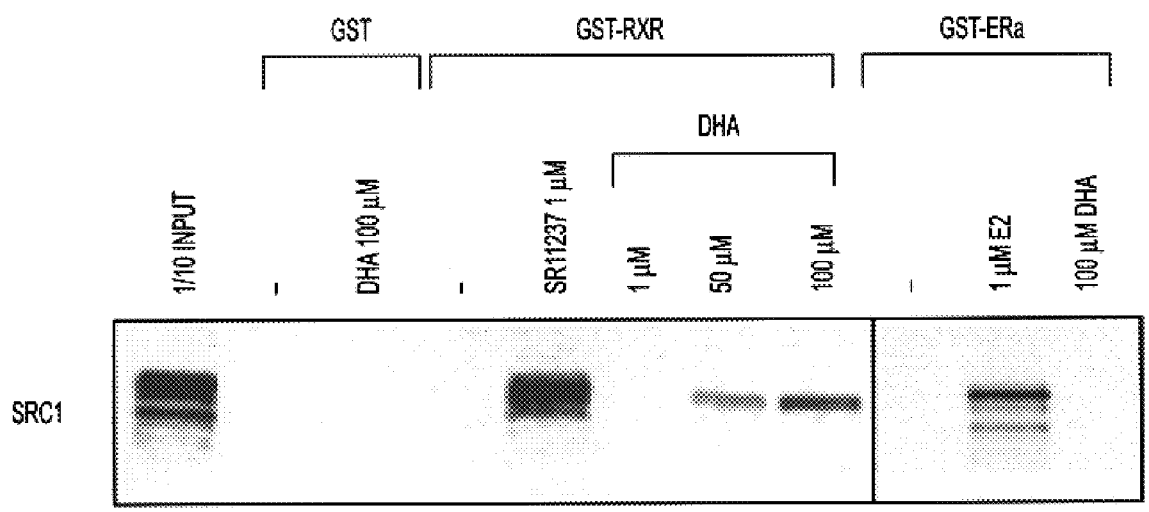
FIG. 4 shows the results of protein binding studies when using docosahexaenoic acid.

The results are set forth in FIG. 4. They show that the bacterially expressed, ligand binding domain of RXR associated efficiently with [$^{35}$S] methionine labelled SRC-1 fragment, when DHA was present, but not when absent. This indicates that DHA binds directly to the RXR ligand binding domain, leading to efficacious interaction with SRC-1.

The foregoing examples show that docosahexaenoic acid, or "DHA" has been identified as a naturally occurring ligand for the retinoid X receptor, or "RXR." This permits the artisan of ordinary skill to determine if a particular substance is an antagonist or agonist to RXR. In brief, this can be determined by combining the material of interest with the receptor, or a molecule which includes the ligand binding domain thereof, and DHA. As DHA is a ligand for RXR, one can compare the binding of DHA to the target molecule, with and without the molecule of interest. In this way, it can be determined if the molecule does in fact bind to RXR. Further, by comparing the effect that the molecule has on the RXR molecule, one can determine whether it is or is not an agonist or antagonist.

The system described herein can be used, in both cell and cell free milieux. Cell free systems are well known, and need not be described herein. These can be used to determine the activity of a molecule of interest, in a fashion similar to that described in the examples, supra, using transfected cells.

Similarly, the recognition that DHA binds as a ligand to RXR suggests an approach to determining molecules of therapeutic value in treating and/or controlling situations wherein regulation of RXR is desired. By utilizing the same techniques for identifying antagonists or agonists, one can determine a therapeutically useful material that can be used either to inhibit RXR, or to stimulate it, or the receptor's effect. Exemplary of conditions where one would use DHA to increase signaling are diabetes and breast cancer. See, e.g., Mukeherjee, et al, Nature 386:407–410(1997); Gottardis, et al. Canc. Res. 56:5566–70(1996), which show that increasing RXR signaling is beneficial in these conditions. Natural DHA or synthetic DHA could be used, with the former being preferred. The fact that RXR is a heterodimerization partner of many nuclear receptors suggests that the administration of the RXR ligand, such as DHA, would provide benefit for treatment of disorders where the up regulation of relevant genes is dependent upon heterodimerization.

It is to be noted that when "RXR" is used herein, any form of the molecule that includes the ligand binding domain, or "LBD" is intended, including the LBD per se, the entire RXR molecule, and molecules of intermediate size, i.e., molecules which include at least the LBD, but not the whole molecule. Also, "LBD" as used herein refers to the minimum portion of the molecule that is required to bind DHA.

"RXR" as used herein, refers to any type of RXR molecule. Mammalian forms, human in particular, are preferred, but other forms, such as murine or other rodent forms, can be used. Also, "DHA" refers to any form of the molecule, such as labelled forms, and so forth.

Other aspects of the invention will be clear to the skilled artisan, and need not be reiterated here.

The terms and expressions which have been employed herein are used as terms of description and not of limitation, and there is no intention in the use of such terms and expressions of excluding any equivalents of the features shown and described or portions thereof, it being recognized that various modifications are possible within the scope of the invention.

We claim:

1. A method for determining if a substance inhibits the binding of docosahexaenoic acid (DHA) to a retinoid X receptor (RXR) comprising contacting said substance with an RXR in the presence of DHA, and determining if said substance inhibits binding of DHA to RXR.

2. The method of claim 1, wherein said inhibition indicates that said substance binds to RXR.

3. The method of claim 1, wherein said RXR is mammalian RXR.

4. The method of claim 1 wherein said mammalian RXR is human RXR.

5. The method of claim 1 wherein said RXR is present on a cell surface.

6. A method of identifying an inhibitor of DHA binding, comprising contacting a substance with an RXR in the presence of DHA, and determining if said substance inhibits binding of DHA to RXR.

* * * * *